US012653388B2

(12) United States Patent
England

(10) Patent No.: US 12,653,388 B2
(45) Date of Patent: *Jun. 16, 2026

(54) CONNECTED MEDICAL DEVICES

(71) Applicant: Boston Scientific Scimed, Inc., Maple Grove, MN (US)

(72) Inventor: Amanda England, Alexandria, VA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/644,285

(22) Filed: Apr. 24, 2024

(65) Prior Publication Data

US 2024/0268643 A1      Aug. 15, 2024

Related U.S. Application Data

(63) Continuation of application No. 17/448,078, filed on Sep. 20, 2021, now Pat. No. 11,992,191.
(Continued)

(51) Int. Cl.
*A61B 1/00* (2006.01)
*A61B 1/012* (2006.01)

(52) U.S. Cl.
CPC ........ *A61B 1/0125* (2013.01); *A61B 1/00009* (2013.01); *A61B 1/0005* (2013.01);
(Continued)

(58) Field of Classification Search
CPC . A61B 1/0125; A61B 1/00009; A61B 1/0005; A61B 1/00066; A61B 1/00114;
(Continued)

(56) References Cited

U.S. PATENT DOCUMENTS

| | | | |
|---|---|---|---|
| 4,192,597 A | 3/1980 | Ting | |
| 4,539,586 A | 9/1985 | Danna et al. | |
| | (Continued) | | |

FOREIGN PATENT DOCUMENTS

| | | | |
|---|---|---|---|
| CN | 103782594 A | 5/2014 | |
| CN | 107278135 A | 10/2017 | |
| | (Continued) | | |

OTHER PUBLICATIONS

International Search Report and Written Opinion issued in International Application PCT/US2021/071508, mailed on Dec. 9, 2021 (13 pages).

*Primary Examiner* — Ryan N Henderson
(74) *Attorney, Agent, or Firm* — Bookoff McAndrews, PLLC

(57) ABSTRACT

A medical assembly may include a first imaging device and a second imaging device. The first imaging device may have a first shaft, a first cable, and a second cable extending from the first handle. The second cable may be in electrical communication with the first cable. A first imager may be disposed at a distal end of the first shaft. The second imaging device may have a second handle, a third cable extending from the second handle, and a second shaft extending distally from the second handle. A second imager may be disposed at a distal end of the second shaft. The first imaging device and the second imaging device may be configured to connect via the third cable, thereby transmitting imaging data from the second imager through the first cable, the second cable, and the third cable.

8 Claims, 6 Drawing Sheets

Related U.S. Application Data

(60) Provisional application No. 63/083,402, filed on Sep. 25, 2020.

(52) U.S. Cl.
CPC ...... *A61B 1/00066* (2013.01); *A61B 1/00114* (2013.01); *A61B 1/00124* (2013.01)

(58) Field of Classification Search
CPC ............ A61B 1/00124; A61B 1/00011; A61B 1/00018; A61B 1/00181; A61B 1/00194
See application file for complete search history.

(56) References Cited

U.S. PATENT DOCUMENTS

| | | | | |
|---|---|---|---|---|
| 4,885,635 | A * | 12/1989 | Kimura | A61B 1/05 348/E5.029 |
| 4,947,828 | A * | 8/1990 | Carpenter | A61B 1/07 600/113 |
| 5,178,130 | A * | 1/1993 | Kaiya | A61B 1/042 348/E5.025 |
| 7,922,650 | B2 * | 4/2011 | McWeeney | A61B 1/00071 600/172 |
| 8,235,887 | B2 * | 8/2012 | Bayer | A61B 1/0676 600/113 |
| 8,529,439 | B2 * | 9/2013 | Ito | A61B 1/012 600/172 |
| 8,608,649 | B2 * | 12/2013 | McWeeney | A61B 1/04 600/149 |
| 8,979,736 | B2 * | 3/2015 | Kawaura | G02B 23/2476 604/533 |
| 10,238,272 | B2 * | 3/2019 | Simmons | A61B 1/00128 |
| 11,744,446 | B2 * | 9/2023 | Meguro | A61B 1/0125 600/146 |
| 11,751,753 | B2 * | 9/2023 | Levasseur | A61M 25/0113 606/108 |
| 2005/0119522 | A1 | 6/2005 | Okada | |
| 2006/0287576 | A1 | 12/2006 | Tsuji et al. | |
| 2008/0009720 | A1 | 1/2008 | Schefelker et al. | |
| 2009/0231419 | A1 * | 9/2009 | Bayer | A61B 1/00096 348/76 |
| 2011/0001851 | A1 | 1/2011 | Nakamura | |
| 2015/0057537 | A1 * | 2/2015 | Dillon | A61B 1/0014 600/113 |
| 2016/0089008 | A1 | 3/2016 | Simmons | |
| 2016/0287054 | A1 | 10/2016 | Fujitani | |
| 2019/0059703 | A1 | 2/2019 | Ting | |
| 2019/0133421 | A1 | 5/2019 | Golden et al. | |
| 2020/0154982 | A1 * | 5/2020 | Niwa | A61B 1/00126 |
| 2021/0016060 | A1 * | 1/2021 | Levasseur | A61B 1/00133 |
| 2021/0022587 | A1 | 1/2021 | Meguro et al. | |
| 2021/0145257 | A1 * | 5/2021 | Levinson | A61B 1/00066 |
| 2022/0192471 | A1 * | 6/2022 | Levy | A61B 1/00135 |
| 2022/0354343 | A1 * | 11/2022 | Brechbiel | A61B 1/0052 |

FOREIGN PATENT DOCUMENTS

| | | |
|---|---|---|
| CN | 107819636 A | 3/2018 |
| EP | 1602319 A1 | 12/2005 |
| WO | 2018163498 A1 | 9/2018 |
| WO | 2019202850 A1 | 10/2019 |
| WO | 2021011273 A1 | 1/2021 |

* cited by examiner

CONNECTED MEDICAL DEVICES

CROSS-REFERENCE TO RELATED APPLICATIONS

This application is a continuation of U.S. patent application Ser. No. 17/448,078, filed on Sep. 20, 2021, which claims the benefit of priority from U.S. Provisional Application No. 63/083,402, filed on Sep. 25, 2020, each of which is incorporated by reference herein in its entirety.

TECHNICAL FIELD

This disclosure relates generally to medical device systems. More particularly, at least some embodiments of this disclosure relate to systems including multiple medical devices electrically connected to one another.

BACKGROUND

Oftentimes, physicians utilize both a larger endoscope, e.g., the mother scope, and a smaller endoscope, e.g., the daughter scope, simultaneously to visualize various portions of the anatomy. This may be done by inserting the daughter scope into a port of the mother scope. The daughter scope may be used to traverse and visualize bodily lumens that are otherwise too small for the mother scope to traverse. Typically, both the mother scope and the daughter scope are connected to separate capital units, e.g., controller/processor, to process and display the visualization feeds provided by both scopes. Separate capital units, for each of the scopes, may further require additional monitors, cabling, and connectors, which can clutter and occupy limited space within an operational setting.

SUMMARY OF THE DISCLOSURE

According to an embodiment, a medical assembly may comprise a first imaging device comprising a first handle and a first shaft extending distally from the first handle, a second imaging device comprising a second handle and a second shaft extending distally from the second handle, and an imaging unit, wherein the first imaging device further comprises (1) a first imager at a distal end of the first shaft, (2) a first cable extending from the first handle for connection to the imaging unit, and (3) a first connector, wherein the second imaging device further comprises (1) a second imager at a distal end of the second shaft and (2) a second connector, and wherein the first connector and the second connector are configured to connect, thereby transmitting imaging data from the second imager to the imaging unit via the first cable.

In an embodiment, the first connector may be electrically connected to the first imager, and the second connector is electrically connected to the second imager. The imaging unit may include a single physical unit housing a controller configured to process the imaging data from the first imager and the imaging data from the second imager. The imaging unit may further include at least one display configured to display images from the first imager and images from the second imager simultaneously and/or sequentially. The connection between the first connector and the second connector may be a male-female connection.

In an embodiment, the first connector may be fixed to a body of the first handle, and the second connector is fixed to a body of the second handle. The first connector may be one of a male connector and female connector, and the second connector may be the other of the male connector and the female connector.

In an embodiment, the first imaging device may include a second cable having a first end in electrical communication with the first cable and a second end including the first connector. The second imaging device may further include a tertiary cable extending from the second handle, wherein the tertiary cable includes a first end coupled to the second handle and a second end including the second connector. The first connector may be one of a male connector and female connector, and the second connector may be the other of the male connector and the female connector.

In an embodiment, the imaging unit is not directly connected to the second imaging device. The second imaging device may be electrically connected to the imaging unit via the first cable. The medical assembly may include only one single, physical imaging unit. The first handle may include a port, and the port receives the second shaft of the second imaging device. The first imaging device may be an endoscope.

According to another embodiment, a medical assembly may comprise a first imaging device comprising a first handle, a first shaft, and a first imager at a distal end of the first shaft, and a second imaging device comprising a second handle, including second shaft, and a second imager at a distal end of the second shaft, wherein the first imaging device further comprises (1) a first cable extending from the first handle for connection to an imaging unit, and (2) a first connector fixed to the first handle, the first connector being electrically connected to the first imager, wherein the second imaging device further comprises a second connector coupled to the second handle, the second connector electrically connected to the second imager, and wherein the first connector and the second connector are configured to connect to transmit imaging data from the second imager to the imaging unit via the first cable of the first imaging device. The medical assembly may further comprise the imaging unit, wherein the imaging unit includes a single physical unit housing a controller configured to process the imaging data from the first imager and the imaging data from the second imager, and at least one display configured to display images from the first imager and images from the second imager simultaneously and/or sequentially. The first connector may be one of a male connector and female connector, and the second connector may be the other of the male connector and the female connector. The first handle may include a port, and the port receives the second shaft of the second imaging device.

According to another embodiment, a medical device may comprise a first imaging device comprising a first handle, a first shaft fixed to and extending from the first handle, a first imager fixed to a distal end of the first shaft, and a first cable fixed to the first handle and configured to connect to an imaging unit for processing of image data received from the first imager, wherein the first handle includes a first connector configured to connect to a second connector of a second imaging device to transmit image data from the second device to the imaging unit via the first cable.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DETAILED DESCRIPTION

Figure 1:
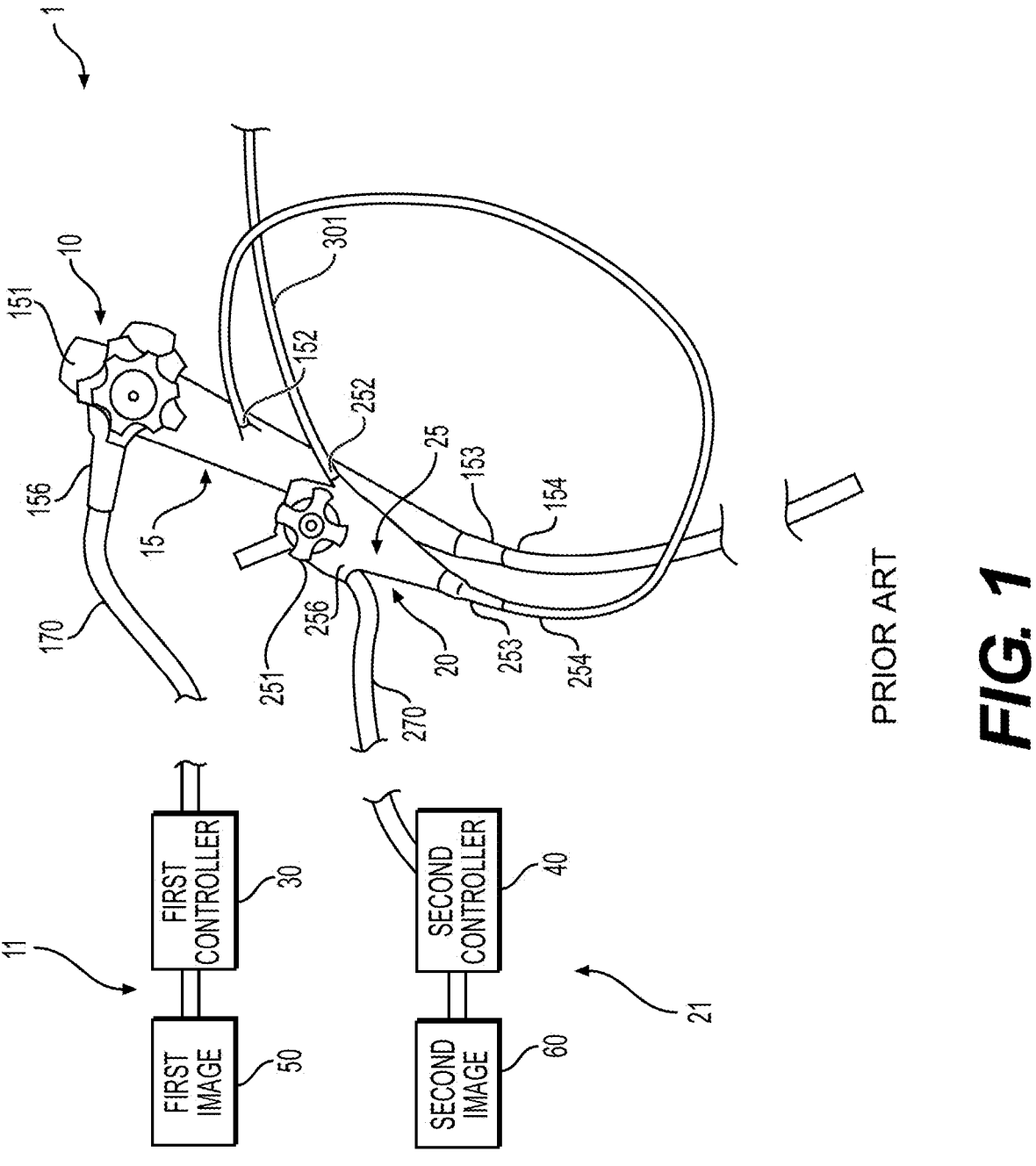
FIG. 1 is a perspective view of a medical system, according to an embodiment.

Reference will now be made in detail to aspects of the disclosure, examples of which are illustrated in the accompanying drawings. Wherever possible, the same or similar reference numbers will be used through the drawings to refer to the same or like parts. The term "distal" refers to a portion farthest away from a user when introducing a device into a subject (e.g., a patient). By contrast, the term "proximal" refers to a portion closest to the user when placing the device into the subject.

Both the foregoing general description and the following detailed description are exemplary and explanatory only and are not restrictive of the features, as claimed. As used herein, the terms "comprises," "comprising," "having," "including," or other variations thereof, are intended to cover a non-exclusive inclusion such that a process, method, article, or apparatus that comprises a list of elements does not include only those elements, but may include other elements not expressly listed or inherent to such a process, method, article, or apparatus. In this disclosure, relative terms, such as, for example, "about," "substantially," "generally," and "approximately," are used to indicate a possible variation of +10% in a stated value or characteristic.

Embodiments of the disclosure may solve one or more of the limitations in the art. The scope of the disclosure, however, is defined by the attached claims and not the ability to solve a specific problem. The disclosure, in certain embodiments, is drawn to a medical system including a first medical device, a second medical device, a connective aspect connecting the first and second medical devices, and a capital unit. The first or second medical device is not particularly limited. Either medical device may be, as an example, any scope (e.g., bronchoscope, duodenoscope, endoscope, colonoscope, ureteroscope, etc.), catheter, tool, instrument, or the like, having a shaft/catheter that extends distally from a handle to a distal portion of the device.

The shaft is not particularly limited, and may be any suitable flexible shaft configured to traverse bodily lumens during a procedure. The shaft may include at least one lumen for receiving any number of additional devices, e.g., scopes, tools, instruments, cables, fluids, or the like.

Similarly, the handle is also not particularly limited, and may be any suitable medical device handle. The handle may include at least one aspect for actuating or controlling the medical device, any tools or devices associated with medical device, and/or the fastening mechanism of the medical device. Moreover, the handle may include at least one port, e.g., a Y-port, in fluid communication with a working channel, e.g., a lumen of the shaft. The port may receive any suitable accessory device, which may extend distally throughout the shaft and towards the distal end of the medical device. The handle may further include an additional port connected to an umbilicus that serves any suitable purpose. For example, said umbilicus may provide wiring between various electronic components housed within the handle, e.g., imaging components, and a capital unit, discussed in further detail below.

The first medical device and the second medical device may be the same or similar devices. For example, the first medical device may be a larger imaging scope, e.g., a mother scope, and the second medical device may be a smaller imaging scope, e.g., the daughter scope. The daughter scope may be inserted through any suitable device port in fluid communication with the working channel, e.g., a lumen, of the shaft of the mother scope. The daughter scope may extend distally through the working channel of the mother scope, and both imaging scopes may simultaneously visualize various portions of the anatomy.

The connective aspect or feature of the mother scope and the daughter scope are not particularly limited. For example, the connective feature may be any suitable mechanism, e.g., an electrical or magnetic interface, that enables the visualization data of both the mother scope and the daughter scope to be transmitted via a single cable/umbilicus, e.g., the umbilicus of the mother scope. For example, connective features may include a male-female connection configured for video output, e.g., HDMI, DisplayPort, or any variation thereof, between the mother scope and the daughter scope. In some embodiments, the connection, e.g., male-female, between both devices may be via components embedded on the handles of both devices. In some other embodiments, the connection, e.g., male-female, between both devices may be via a secondary umbilicus extending from a primary umbilicus, e.g., the umbilicus of the mother scope, and a cable of the daughter scope. The aforementioned connection between the mother scope and the daughter scope may result in only a single cable/umbilicus connected a single capital unit, thereby reducing the need for additional capital units. It is noted that the connection between both devices is not limited to male-female connections, and other connective means may be used as well. For example, other connective means may include plug and socket connections, serial port connections, coaxial connections, USB connections, Ethernet connections, and other similar connective types. Another example of a connective means may be exposed wire leads of one device connecting to or contacting reciprocal receiving pads embedded in the handle of the other device. The contact point between the two devices may transmit video signals from one device to the other.

The capital unit, also referred to as an imaging unit, is not particularly limited, and may include at least any suitable controllers/processors and a display component. The imaging unit may be a single, physical unit housing said processors, controllers, etc. for processing imaging data provided by the imaging components of the mother scope and the daughter scope. The display component may be electrically coupled to the housing and the housed processors/controllers. The display may be only one monitor that receives and exhibits the imaging feeds from both devices, either displayed simultaneously or sequentially. In some embodiments, multiple monitors may be used to display individual images. The imaging unit will further include any suitable memory and software/hardware needed for image processing. The imaging unit may also include software/hardware to control or help control irrigation, aspiration, or other functions of the medical devices/scope. The imaging unit may include connection for power as well.

FIG. 1 illustrates an embodiment of a medical system without the connective features discussed above. Medical system 1 includes a first medical device 10, a second medical device 20, a first capital unit 11, and a second capital unit 21. First medical device 10 includes a flexible shaft 154 (e.g., a catheter) and a handle 15 connected to a proximal end of flexible shaft 154. Handle 15, or some other device for actuating or controlling first medical device 10 and any tools or devices associated with medical device 10, includes an actuating device 151. Actuating device 151 controls articulation of flexible shaft 154, and/or an articulation joint at a distal end of flexible shaft 154, in multiple directions. Device 151 may be, for example, one or more rotatable knobs that each rotates about its axis to push/pull actuating elements, e.g., steering wires (not shown). The actuating elements, such as cables or wires suitable for medical procedures (e.g., medical grade plastic or metal), extend distally from a proximal end of medical device 10 and connect to a distal portion of flexible shaft 154 to control movement thereof. Alternatively, or additionally, a user may operate actuating elements independently of handle 15. Distal ends of actuating elements may extend through flexible shaft 154 and terminate at an articulation joint and/or a distal tip of flexible shaft 154. For example, one or more actuating elements may be connected to an articulation joint, and actuation of actuating elements may control the articulation joint or the distal end of flexible shaft 154 to move in multiple directions (e.g. up/down and or left/right).

In addition, one or more electrical cables (not shown) may extend from the proximal end of medical device 10 to the distal end of flexible shaft 154 and may provide electrical controls to imaging, lighting, and/or other electrical devices at the distal end of flexible shaft 154, and may transmit imaging signals from the distal end of flexible shaft 154 proximally to be processed and/or displayed on a display of first capital unit 11 (discussed below). Handle 15 may also include ports 152, 156 for introducing and/or removing tools, fluids, or other materials from the patient. As shown in FIG. 1, port 152 receives a shaft 254 of second medical device 20 (described in further detail below). Port 156 is connected to a first umbilicus 170 for wiring of the electronic components housed within handle 15 to first capital unit 11. Furthermore, medical device 10 may include a strain relief 153 that is attached to a distal end of handle 15. Strain relief 153 may be a cover of any suitable soft material that tapers distally and has an opening for shaft 154 at its distal end. Strain relief 153 is not particularly limited, and may assist in preventing shaft 154 from kinking.

Second medical device 20 is similar to first medical device 10, as device 20 includes various similar components. Like first medical device 10, device 20 includes a flexible shaft 254 and a handle 25 connected to a proximal end of flexible shaft 254. As discussed above, shaft 254 is inserted into port 152 of device 10, and extends distally throughout a working channel, e.g., a lumen of shaft 154 (not shown). Handle 25 includes an actuating device 251, which may also be one or more rotatable knobs that each rotates about its axis to push/pull actuating elements, e.g., steering wires (not shown), extending through device 20. Device 20 may also include one or more electrical cables (not shown) providing electrical controls to imaging, lighting, and/or other electrical devices at the distal end of flexible shaft 254, and may transmit imaging signals from the distal end of flexible shaft 254 proximally to be processed and/or displayed on a display of first capital unit 21 (discussed below). Handle 25 also includes ports 252, 256 for introducing and/or removing tools, fluids, or other materials from the patient. Port 252 may be used to introduce an accessory device 301, which may be any suitable tool or device for medical purposes. Port 256 is connected to a second umbilicus 270 for wiring of the electronic components housed within handle 25 to second capital unit 21.

It is noted that system 1 is without any electrical connection between device 10 and device 20, thereby requiring two separate capital units, e.g., unit 11 and unit 21. Device 10 and device 20 may be physically held or fixed together by any suitable means, e.g., a strap. For example, devices 10 and 20 may be held together by any attachment structure disclosed in U.S. Patent Application Publication No. 2019/0133421, the complete disclosure of which is incorporated by reference herein.

First capital unit 11 includes a first controller 30 and a first image/display 50. First controller 30 is coupled to the proximal end of umbilicus 170. Controller 30 may be any suitable controller configured to process the imaging data provided by the imaging components of first medical device 10. First image/display 50 is not particularly limited, and may be any suitable display or monitor exhibiting the imaging feed/data received by device 10 and processed by controller 30. First image 50 may be electrically wired to controller 30, or may be wirelessly connected in some instances.

Second capital unit 21 includes a second controller 40 and a second image/display 60. Second controller 30 is coupled to the proximal end of umbilicus 270. Controller 40 may also be any suitable controller configured to process the imaging data provided by the imaging components of second medical device 20. Second image/display 60 is not particularly limited, and may be any suitable display or monitor exhibiting the imaging feed/data received by device 20 and processed by controller 40. Second image 60 may be electrically wired to controller 40, or may be wirelessly connected via any suitable manner.

Figure 2A:
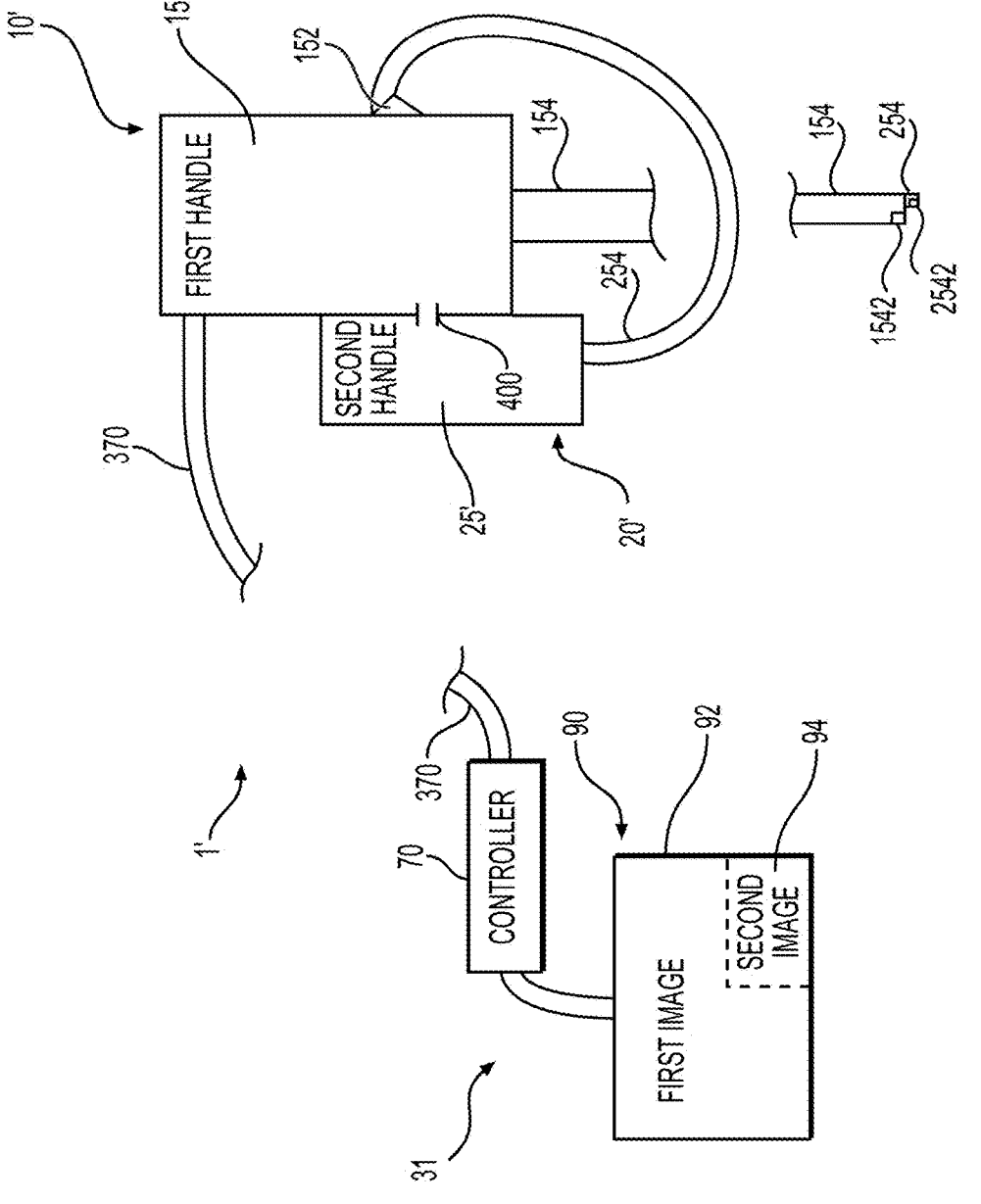
FIG. 2A is a perspective view of a medical system, according to another embodiment.
Figure 3A:
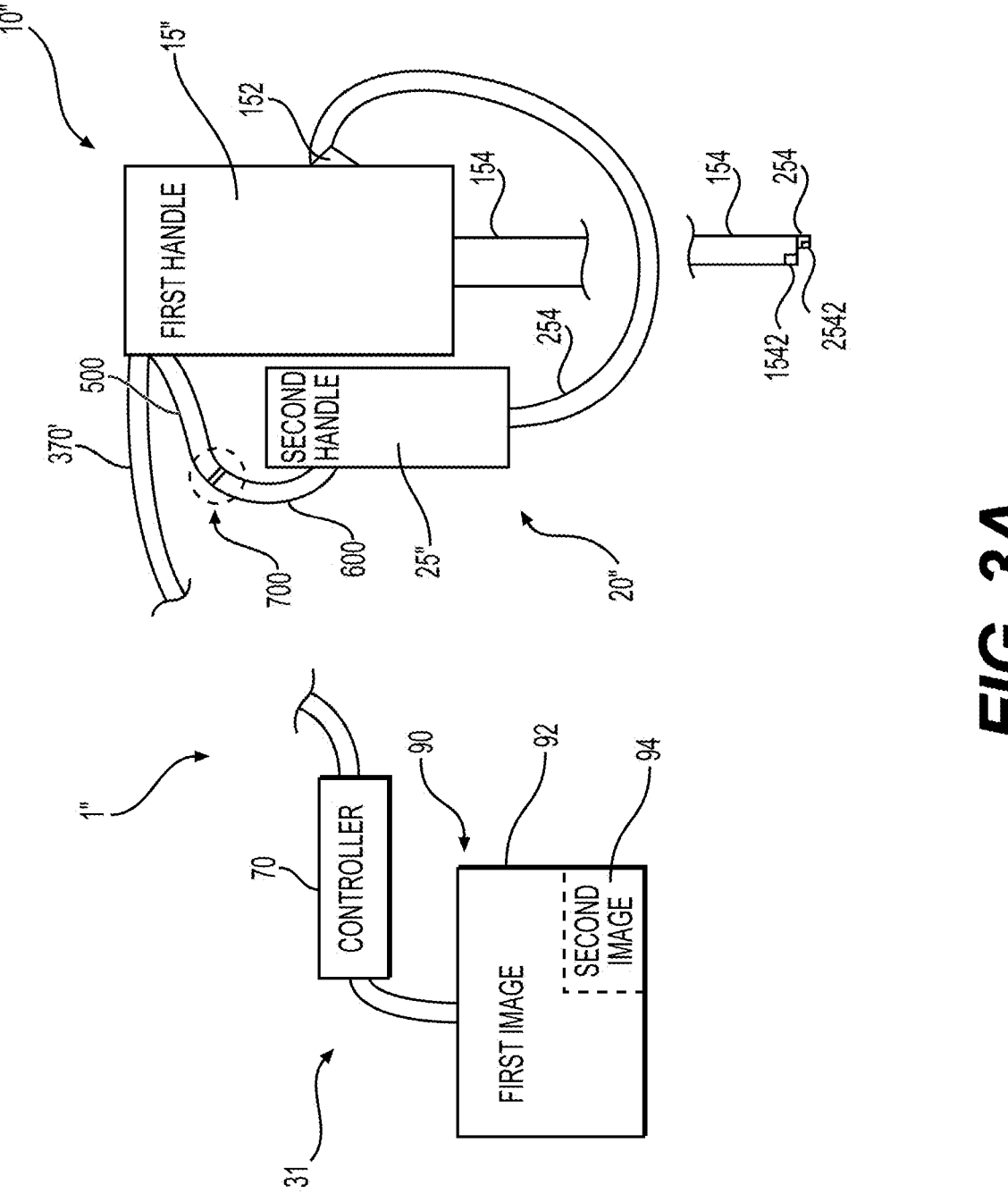
FIG. 3A is a perspective view of a medical system, according to another embodiment.

The presence of both unit 11 and unit 21 increases the amount of machinery within an operational setting, and reduces the amount of space that may be utilized for other purposes. The following medical system embodiments illustrated in FIGS. 2A and 3A provide alternative systems including a connective feature between first medical device 10 and second medical device 20. As discussed above, said electrical connection between device 10 and device 20 removes a second capital unit from the system, thereby providing additional space within a setting.

FIG. 2A illustrates another embodiment of a medical system, e.g., medical system 1'. Like reference numerals refer to like parts. System 1' includes first medical device 10', second medical device 20', and a capital unit 31. It is noted that first medical device 10' includes all the features discussed above with respect to device 10, e.g., umbilicus 370. Second medical device 20' likewise includes all the features discussed above with respect to device 20, except device 20' may be without an umbilicus. Furthermore, device 10' and device 20' may be electrically connected at a connection point 400 via any suitable components embedded onto or otherwise fixed to handle 15' and handle 25'. The electrical connection between device 10' and device 20' is not particularly limited, and may be by any suitable means, e.g., a male-female connection. Examples of the connective components are further discussed below when referring to FIGS. 2B-2C. Said connection at point 400 enables the visualization data of both device 10' and device 20' to be transmitted to a single capital unit 31, via a single umbilicus 370 extending from handle 15'. Note that, inside an outer housing of handle 15' will be electrical components, including wiring, cabling, and/or circuit boards, to convey the image data from device 20' to umbilicus 370, and ultimately to capital unit 31.

Capital unit 31 is not particularly limited. Unit 31 includes a controller 70 and a display 90 connected to controller 70. Controller 70 is coupled to the proximal end of umbilicus 370. Controller 70 may be any suitable controller configured to process the imaging data provided by the imaging components of both first medical device 10' and second medical device 20'. Display 90 is not particularly, and may be any suitable display or monitor exhibiting the imaging feeds/data received by devices 10', 20', and processed by controller 70. As shown, display 90 may show both a first image 92 and a second image 94 simultaneously, without requiring a second display or a second controller. One or more of handle 15', device 20', and controller 70 may include a user input to control which image feed is being displayed or whether both image feeds are displayed.

Figure 4:
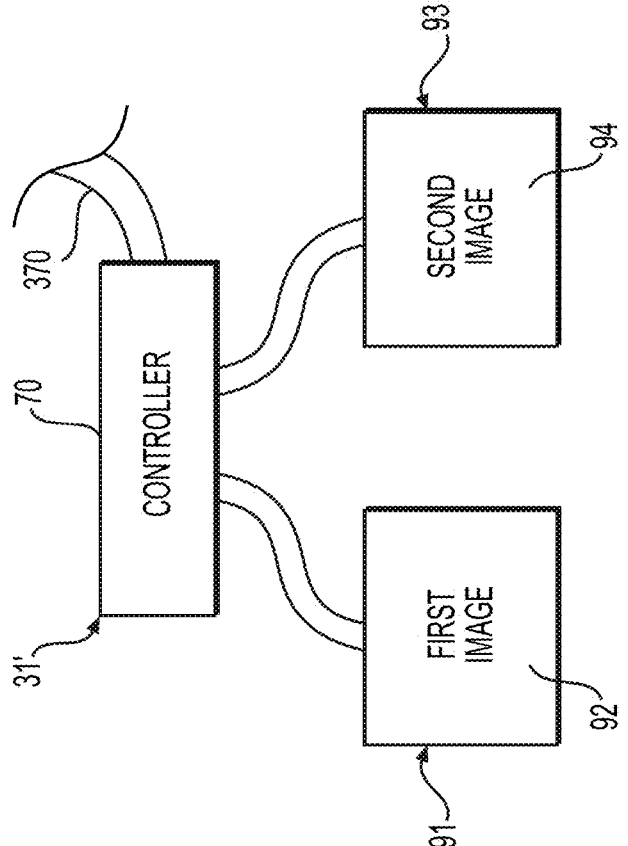
FIG. 4 is a perspective view of a capital unit, according to another embodiment.

It is noted that a capital unit is not limited to a single display. In other embodiments, as shown in FIG. 4, capital unit 31' may still include a single controller 70, but controller 70 may be connected to two displays 91 and 93. Display 91 may show first image 92, and display 93 may show second image 94. Thus, a user may implement a capital unit 31, 31' including a single display 90 or multiple displays 91, 93 based on the user's preference.

Figures 2B, 2C:
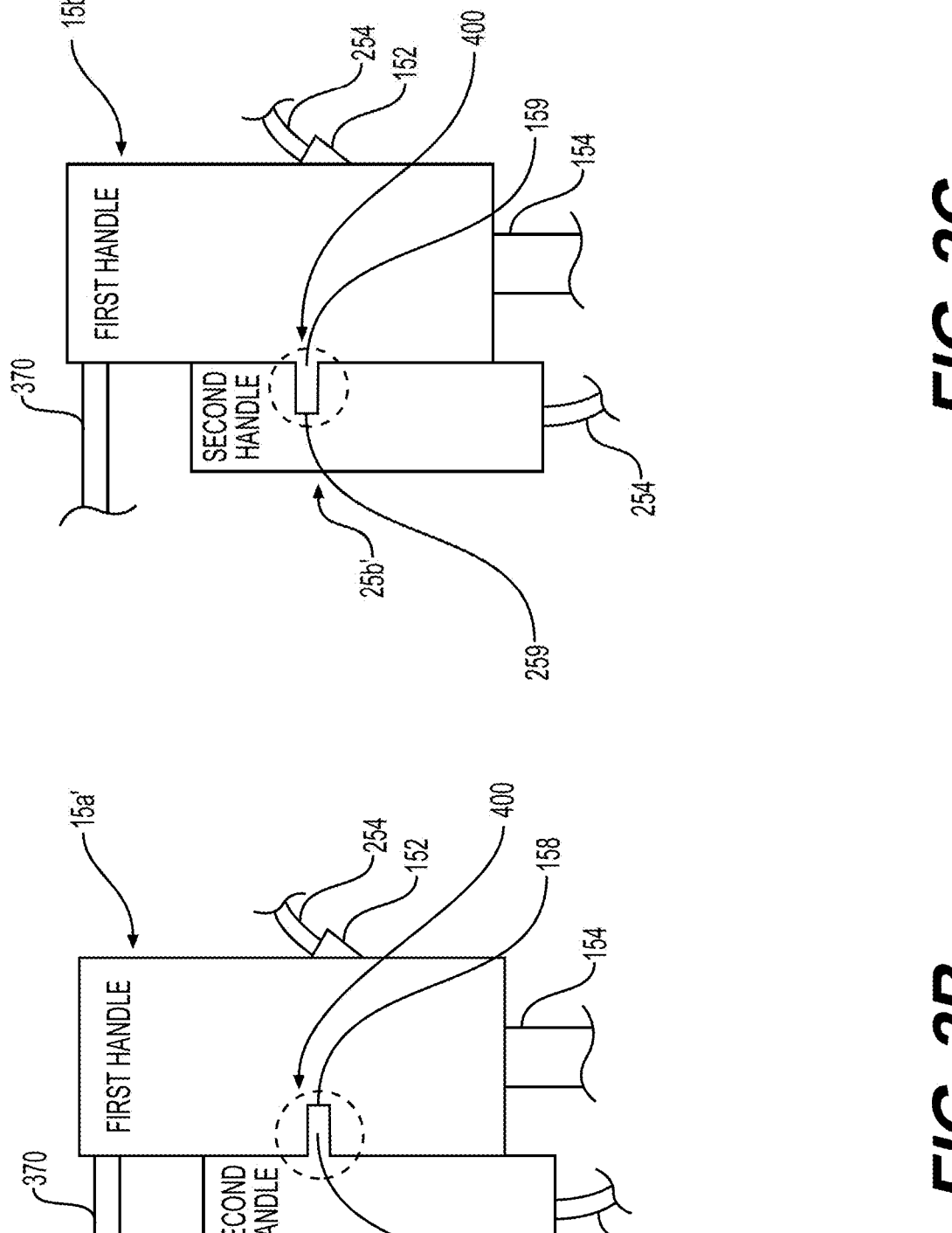
FIGS. 2B-2C are views of a connection between devices of the medical system of FIG. 2A.

Referring to FIG. 2B, handle 15' (now identified as 15a') of device 10' may include a receiving aspect 158, e.g., a female connector, embedded onto or otherwise fixed to handle 15a'. Receiving aspect 158 is not particularly limited, and may be any suitable electrical receiving component. Receiving aspect 158 is also not limited with respect to where it may be positioned on handle 15a' though in some embodiments it may be positioned to receive a corresponding aspect of handle 25a' so that handle 25a' is in an ergonomically suitable position and orientation for use by a medical practitioner. Handle 25' (now identified as 25a') of device 20' may include a connective aspect 258, e.g., a male connector, embedded onto or otherwise fixed to handle 25a'. Connective aspect 258 is not particularly limited, and may be any suitable male connector. Connective aspect 258 may protrude from handle 25a' or may be coupled to handle 25a' in a pivotable manner. Examples of connective types may include HDMI, DisplayPort, any other connector mentioned in this disclosure, any similar variation thereof, or any other suitable connector now know or developed in the future. Thus, FIG. 2B illustrates an example in which connective aspect 258 of device 20' may be connected to receiving aspect 158 of device 10'. FIG. 2C illustrates an alternative connection in which handle 25' (now identified as 25b') includes a receiving aspect 259, e.g., a female connector, embedded onto or otherwise fixed to handle 25b'. Handle 15' (now identified as 15b') of device 10' includes connective aspect 159, e.g., a male connector, embedded onto or otherwise fixed to handle 15b'. Thus, FIG. 2C illustrates an example in which connective aspect 159 of device 10' may be connected to receiving aspect 259 of device 20'.

Referring to the FIGS. 2A-2B discussed above, a method of using medical system 1' is discussed. A user may connect first imaging device 10' to the housing of capital unit 31 by connecting umbilicus 370 to any suitable receiving component (not shown) of capital unit 31. This connection may also connect device 10' to various components of capital unit 31, including controller 70. The user may deliver device 10' into the body of a subject, via a natural orifice (such as a mouth or anus) and through a tortuous natural body lumen of the subject, such as an esophagus, stomach, colon, etc. Device 10' may be delivered while transmitting image data from a first imager 1542 at a distal tip of device 10', to handle 15', to umbilicus 370, and ultimately to capital unit

31, which processes image data via controller 70 and displays an image feed 92 from device 10' onto a display 90, e.g., a monitor. The user may electrically connect second device 20' to first device 10' by connecting connective aspect 258 of device 20' to receiving aspect 158 of device 10'. Alternatively, the user may electrically connect second device 20' to first device 10' by connecting connective aspect 159 of device 10' to receiving aspect 259 of device 20'. The user may insert shaft 254, including a second imager 2542 at its distal end, through port 152 of first device 10', thereby extending shaft 254 distally throughout shaft 154. Given the aforementioned electrical connection between first device 10' and second device 20', image data from second imager 2542 of second device 20' may be transmitted through the aforementioned connective/receiving aspects of device 10' and device 20', to umbilicus 370, to controller 70, and displayed onto monitor 90.

FIG. 3A illustrates another embodiment of a medical system, e.g., medical system 1". Like reference numerals refer to like parts. System 1" includes first medical device 10", second medical device 20", and a capital unit 31. It is noted that first medical device 10" includes all the features discussed above with respect to device 10, e.g., umbilicus 370', first imager 1542, second imager 2542, etc. However, device 10" may further include a secondary umbilicus 500 extending from umbilicus 370' or a portion of handle 15" that ultimately is in electrical communication with umbilicus 370'. A proximal end of umbilicus 500 may include a connective feature, discussed in further detail when referring to FIGS. 3B-3C.

Second medical device 20" likewise includes all the features discussed above with respect to device 20. Device 20" includes a tertiary umbilicus 600 that connects the wiring of the electronic components housed within handle 25" and or otherwise within device 20" to a connective feature on the proximal end of umbilicus 600. Secondary umbilicus 500 and tertiary umbilicus 600 may electrically connect at a connection point 700. The electrical connection between umbilicus 500 and umbilicus 600 is not particularly limited, and may be by any suitable means, e.g., a male-female connection, including any of the connectors mentioned herein. Through such connection, imaging data from device 20" is transmitted to umbilicus 500 and ultimately to primary umbilicus 370', which in turn transmits said data to capital unit 31. Examples of the connective components are further discussed below when referring to FIGS. 3B-3C.

Capital unit 31 is not particularly limited. Unit 31 includes a controller 70 and a display 90 connected to controller 70. Controller 70 is coupled to the proximal end of primary umbilicus 370'. Controller 70 may be any suitable controller configured to process the imaging data provided by the imaging components of both first medical device 10" and second medical device 20". Display 90 is not particularly, and may be any suitable display or monitor exhibiting the imaging feeds/data received by devices 10", 20", and processed by controller 70. As shown, display 90 may show both a first image 92 and a second image 94 simultaneously, without requiring a second display or a second controller. Furthermore, as discussed above when referring to FIG. 4, a capital unit, e.g., capital unit 31', is not limited to a single display, but may include a single controller 70 and two displays 91 and 93. Display 91 may show first image 92, and display 93 may show second image 94. Thus, a user may implement a capital unit 31, 31' including a single display 90 or multiple displays 91, 93 based on the user's preference. One or more of handle 15", device 20", and controller 70 may include a user input to control which image feed is being displayed or whether both image feeds are displayed.

Figure 3C:
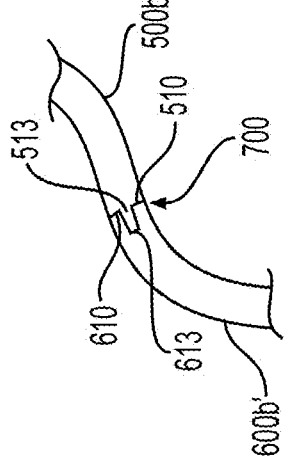
FIGS. 3B-3C are views of a connection between devices of the medical system of FIG. 3A.
Figure 3B:
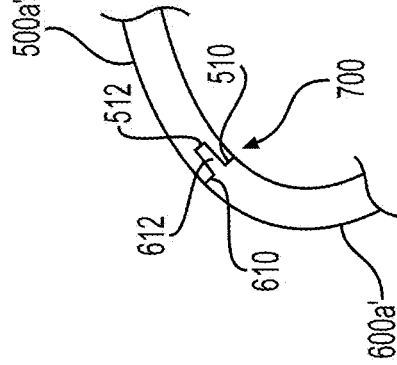

Referring to FIG. 3B, a proximal end 510 of secondary umbilicus 500 (now identified as 500*a*') may include a receiving aspect 512, e.g., a female connector. Receiving aspect 512 is not particularly limited, and may be any suitable electrical receiving component. A proximal end 610 of tertiary umbilicus 600 (now identified as 600*a*') of device 20" may include a connective aspect 612, e.g., a male connector. Connective aspect 612 is not particularly limited, and may be any suitable male connector. Connective aspect 612 may protrude proximally and may be received by receiving aspect 512, so that proximal end 510 and proximal end 610 may be adjacent or flush against, and electrically connected to, one another. Examples of connective types include any of the connected mentioned herein. Thus, FIG. 3B illustrates an example in which connective aspect 612 of umbilicus 600*a*' of device 20" may be connected to receiving aspect 512 of umbilicus 500*a*' of device 10".

FIG. 3C illustrates an alternative connection in which tertiary umbilicus 600 (now identified as 600*b*') includes a receiving aspect 613, e.g., a female connector, at proximal end 610. Secondary umbilicus 500 (now identified as 500*b*') includes connective aspect 513, e.g., a male connector, at proximal end 510. Thus, FIG. 3C illustrates an example in which connective aspect 513 of umbilicus 500*b*' of device 10" may be connected to receiving aspect 613 of umbilicus 600*b*' of device 20".

The method of using medical system 1" may be the same or similar to the method of using system 1', discussed above. However, when using medical system 1", a user may electrically connect second device 20" to first device 10" by connecting connective aspect 612 of device 20" to receiving aspect 512 of device 10". Alternatively, the user may electrically connect second device 20" to first device 10" by connecting connective aspect 513 of device 10" to receiving aspect 613 of device 20".

It will be apparent to those skilled in the art that various modifications and variations can be made to the disclosed device without departing from the scope of the disclosure. Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A medical assembly, comprising:
a first imaging device having:

a first handle;
a first cable and a second cable, each extending from the first handle, wherein the second cable is in electrical communication with the first cable; and
a first shaft extending distally from the first handle, wherein a first imager is disposed at a distal end of the first shaft;
a second imaging device, having:
a second handle;
a third cable extending from the second handle; and
a second shaft extending distally from the second handle, wherein a second imager is disposed at a distal end of the second shaft; and
wherein the first imaging device and the second imaging device are configured to connect via the third cable, thereby transmitting imaging data from the second imager through the first cable, the second cable, and the third cable.

2. The medical assembly of claim 1, wherein the third cable is configured to connect to the second cable via a connector.

3. The medical assembly of claim 2, wherein the connector includes a male connector disposed on one of the second cable or the third cable, and wherein the connector further includes a female connector disposed on the other of the second cable or the third cable.

4. The medical assembly of claim 1, wherein the first handle includes a port, wherein the port is configured to receive the second shaft.

5. The medical assembly of claim 1, further comprising an imaging unit, wherein the first cable is configured to connect to the imaging unit.

6. The medical assembly of claim 5, wherein the imaging unit includes a single physical unit housing a controller configured to process imaging data from each of the first imaging device and the second imaging device.

7. The medical assembly of claim 6, wherein the imaging unit further comprises a first display, wherein the first display is configured to display one or both of the imaging data from the first imaging device and the second imaging device.

8. The medical assembly of claim 7, wherein the imaging unit further comprises a second display, wherein the first display is configured to display imaging data from the first imaging device, and wherein the second display is configured to display imaging data from the second imaging device.

* * * * *